(12) United States Patent
Hock

(10) Patent No.: US 6,487,906 B1
(45) Date of Patent: Dec. 3, 2002

(54) FLEXIBLE FILM SENSOR SYSTEM FOR MONITORING BODY MOTION

(75) Inventor: Allan G. Hock, Londonderry, NH (US)

(73) Assignee: Advantedge Systems Inc, Londonderry, NH (US)

(*) Notice: Subject to any disclaimer, the term of this patent is extended or adjusted under 35 U.S.C. 154(b) by 49 days.

(21) Appl. No.: 09/663,488

(22) Filed: Sep. 18, 2000

(51) Int. Cl.⁷ .............................. A61B 5/22
(52) U.S. Cl. ................................. 73/379.01
(58) Field of Search ............... 73/379.01, 379.02, 73/379.03, 379.07, 379.08, 379.09; 600/547

(56) References Cited

U.S. PATENT DOCUMENTS

| | | | |
|---|---|---|---|
| 4,108,164 A | 8/1978 | Hall, Sr. | |
| 4,665,388 A | 5/1987 | Ivie et al. | |
| 4,667,685 A | 5/1987 | Fine | |
| 4,986,280 A | 1/1991 | Marcus et al. | |
| 5,064,192 A | * 11/1991 | Smith | 482/8 |
| 5,146,929 A | 9/1992 | Sawhill | |
| 5,260,689 A | * 11/1993 | Meyers et al. | 340/521 |
| 5,316,017 A | * 5/1994 | Edwards et al. | 600/595 |
| 5,354,050 A | 10/1994 | McCarthy | |
| 5,375,610 A | 12/1994 | La Course et al. | |
| 5,607,361 A | 3/1997 | Mastandrew et al. | |
| 5,724,990 A | * 3/1998 | Ogino | 600/587 |
| 5,797,803 A | 8/1998 | Jung | |
| 5,823,886 A | 10/1998 | Murray | |
| 6,032,530 A | * 3/2000 | Hock | 600/595 |
| 6,060,046 A | * 5/2000 | Goll | 424/78.09 |

OTHER PUBLICATIONS

Spine Tuner Instructions, Clear Sky Products 1997, Rev 5,1,97.

* cited by examiner

Primary Examiner—Max Noori
(74) Attorney, Agent, or Firm—Vernon C. Maine; Maine & Asmus

(57) ABSTRACT

A sequence of low force, high compliance, long extension, piezofilm-based sensors for a biofeedback system for self-monitoring of selected body motions. Flexible, large area, piezofim sensors are mounted on compliant but less flexible, larger area, backbone structures so as to distribute localized stress anomalies and produce a useful, coherent, signal voltage for realtime body motion monitoring. The sensors are used in combination with body appliances that permit suitable placement of the sensors proximate the body, in areas suitable for measuring body motion, such as twist, stretch and flexure. The sensors provide input signals to a small, self contained signal processing and feedback module that generates a limited sequence of stepped announcements indicating the amount of motion detected. Instant feedback is provided to the user in the form of audible tones, colored lights, or other means intended to provide periphery feedback without directly interferring with the intended motion.

22 Claims, 13 Drawing Sheets

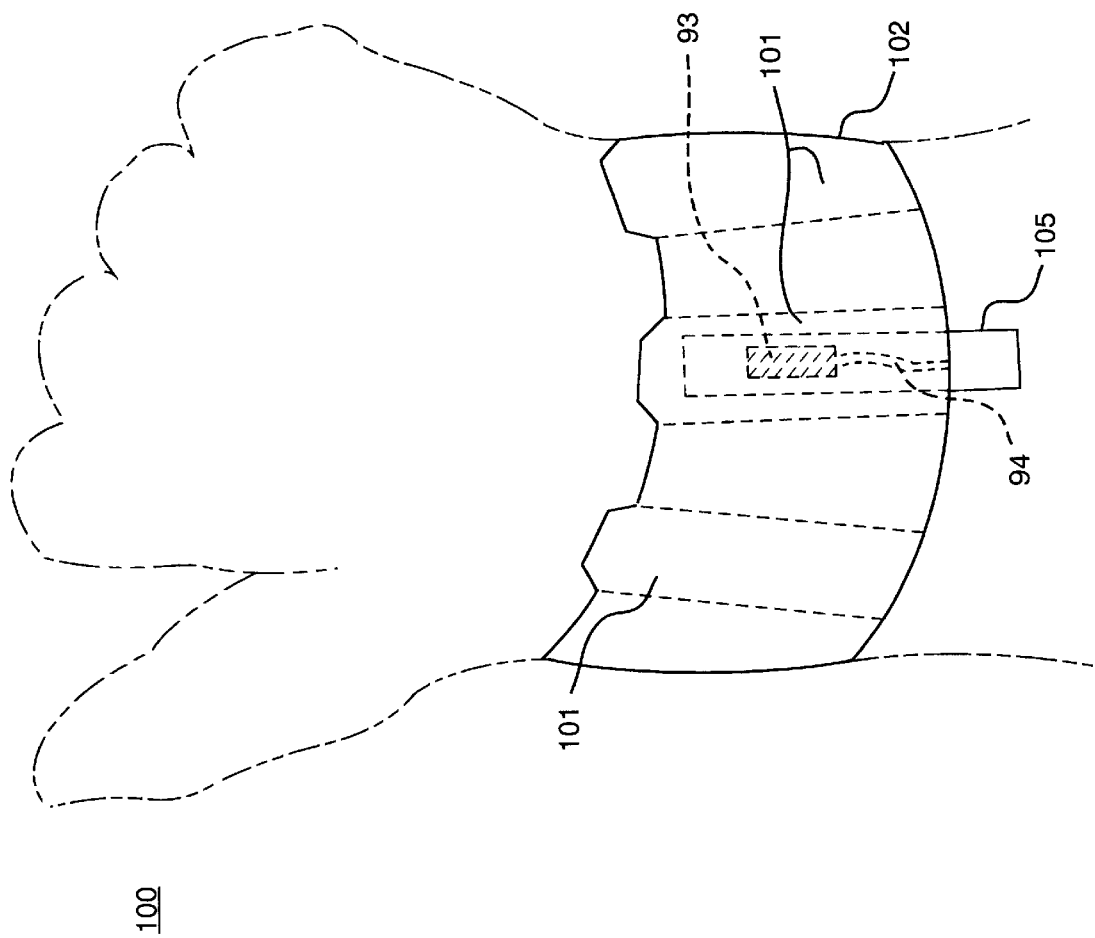

FLEXIBLE FILM SENSOR SYSTEM FOR MONITORING BODY MOTION

This application relates to U.S. Pat. Nos. 5,745,028, issued Apr. 28, 1998, and 6,032,530, issued Mar. 7, 2000, and pending U.S. application Ser. No. 09/084,440, filed May 22, 1998.

BACKGROUND OF THE INVENTION

1. Technical Field of the Invention

This invention relates to instrumentation for monitoring of motion and flexure of body joints and digits. In particular, it relates to flexible film based sensor configurations for monitoring body joint movement, suitable for use with body-mounted appliances and specialized signal processors with discrete audible or colored light and other biofeedback capabilities.

2. Discussion of Prior Art

The art of user figment with medical devices for injury avoidance and rehabilitation therapy is not new. However, as with medical care and treatment in general, it used to be conducted with a somewhat cavalier attitude about cost. The 'if it doesn't cost a lot in can't be any good' attitude, was driven home to the applicant some years ago when a new state of the art oscillometer product costing a conservative (US)$300 was offered to a surgeon who quipped, "I paid that for the light I wear in the operating room," and declined to consider it further.

Now, however, we have entered an era of greater emphasis on reduction and control of medical care and treatment costs. There is a new willingness by the medical care delivery establishment to consider and even search for lower cost products that offer bonafide medical benefits. The need for lower cost medical products extends to injury prevention and rehabilitation devices.

There are, in the prior art, body suit implementations for general measurement of body activities for injury avoidance training and/or physical rehabilitation. One body suit, disclosed in U.S. Pat. No. 4,729,377, requires points of electrode contact with the skin and requires soaking the garment with conductive fluid to select the measurement points of interest. Another suit, disclosed in U.S. Pat. No. 5,375,610, encompasses the entire body and measures inclination by a plurality of mercury switches. Both are costly examples of accomplishing generalized monitoring at the expense of ease of use, and do not lend themselves to casual use as in sports training or for prolonged use in repetitive or continuous motion. These types of devices are more appropriate for specific data collection testing sessions rather than for everyday wearing to monitor body motion for injury prevention or rehabilitation in the industrial setting.

Many prior art devices utilize standard transducer technology that is rigid and has low electrical sensitivity. The former creates a comfort issue when integrated with a user system while the latter generates a need for electrical shielding and high gain amplification, limiting both cost and function.

In addition to the medical need, professional and recreational training activities for kinetic sports share the requirement for low cost, effective monitoring of body motion. Common problems facing both industries are the need for a system or inventory of low cost associated devices to meet the needs of athletes and patients of different sizes; the need for a flexible scheme for universal figments adaptable to each part of the body; the need for a self-monitoring system and methodology that is easy for the athlete or patient to remove and reinstall daily, and to use and interpret so as to realize the full benefit.

More specifically, industry data clearly indicates a large amount of pain, suffering, lost time and lost productivity results from back injuries that occur on and off the job from lack of training or improper training and monitoring in lifting and related activities. Lifting is a general problem, while twisting while lifting or repetitive twisting such as when moving parts along a production line are also statistically very significant contributors to employee injuries.

One example of a recently introduced commercial body motion monitoring device is the Spine Tuner™ by Clear Sky Products, a posture monitor consisting of a belt that goes around the back approximately half way between the waist and shoulder that holds a small system module against the spine. The system module consists of a pressure-activated switch that is actuated by pressure, forcing the housing to compress front to back, actuating the switch. When the switch is closed, a battery is connected directly to a small motor with unbalanced weight, to cause vibrations that are noticeable to the user. Adjusting the contact spacing on a stamped metal switch by turning an adjustment screw sets the system sensitivity. This operation cannot be performed while the device is being worn, which requires the user to use an awkward trial and error approach to obtain a useful setting. The feedback scheme for the Clear Sky device utilizes a single threshold at which a signal is initiated.

An example of the need for body motion monitoring in the sports training category is the game of golf. The new buzzword in the golf industry for the past five years or so is the "X" factor, a rotation of the shoulders relative to the hips. The need to monitor spinal twisting in this instance is similar to some industrial requirements.

It is common for workers in some companies and industries to be required to wear back support belts. Home Depot and the Marriott Chain are among companies believed to require the use these devices for employees in lift-related jobs. Interviews with workers that are required to wear these belts have produced comments such as, "Now that I have support I can lift heavier things", which defeats the primary purpose; and "I have to wear it but I don't think it does anything." There seems to be an acceptance and confidence problem with these commonly required devices that defeats or reduces their intended benefit.

Much of the technology for medical and sports requirements rely on braces. A sport brace called The Secret™, endorsed by golf pro Greg Norman, sells at a premium price, but constrains the user to a particular position of the wrist, an approach that is not likely to promote good muscle memory.

Braces in general have a number of problems, they are uncomfortable, frequently they do not quite fit the subject or the need, in training they do not promote good muscle memory, they can cause injury by constraining too well during a required activity, particularly in athletics, and they can promote "false" confidence causing users to try to over perform. When these devices are removed, everyday performance seems awkward.

What is needed, for both medical and athletic fields, is a low cost system and methodology of devices, sensors and biofeedback mechanisms that are flexible and adaptable to various body motions, comfortable to wear, and easy to understand and use.

SUMMARY OF THE INVENTION

Our research, as disclosed in this and previously filed applications, shows that discrete, multi-level thresholds of realtime biofeedback, where the feedback mechanism holds the peak a value of the measured parameter sufficiently long or otherwise emphasizes it to ensure user awareness, enables more meaningful comprehension of the relationship between the effort and the motion response. A limited set of frequency-discrete tones of audio feedback, or of color discrete light feedback, accomplish this end.

Not all means of sensory awareness are suitable for this more complex type of biofeedback. Vibration, for example, as with a mechanical device worn where its physical vibrations are noticeable to the wearer, is known to be viable for single threshold, on/off type signals. However, most users' level of sensitivity to this type of messaging is too low to discriminate between even a limited set of different vibration frequencies or amplitudes, particularly in a realtime environment. Physically displaced points of vibration may be suitable for messages with significantly different meaning, but may be too distracting for usefully tracking the acceleration common to repetitive human movements.

A non-invasive monitoring system with discrete audible or lighted color, used on a repetitive basis, makes it clear that the user is approaching a danger limit, eliminating the over confidence factor and encouraging compliance with proper lifting or other pertinent motion technique, and ultimately teaching the user what effort will generate the best result.

A biofeedback system with unique sensors is herein disclosed that allows for a universal monitoring methodology to be applied to the physical therapy needs for the human body. The system combines configurable mounting appliances, compatible motion sensors, coded means for positioning and orienting sensors at any location of the body, with a small, self-contained signal processing and feedback module. Multi-level instant audible feedback, or multi-level visual feedback such as by a set of different colored LED's or other visual display of discrete colors, is employed to provide a quick learning environment. Motions of the back, torso, limb joints and digits relevant to the general task of concern, can be selected and monitored by the sensors of the invention. Specific embodiments employing the concepts and methodology focus on the back of limb joints, i.e. the elbow, wrist, digits, knee and ankle. Other embodiments are taylored towards proper lifting motion, and on avoiding twisting of the back while lifting or performing common repetitive industrial movements that have a proven history of harming the performer.

Several embodiments of a low force, high compliance, long extension, body motion sensor are disclosed, which strengthen the monitor system concepts,. These enhance the functionality, simplicity and cost of the resulting system implementation. The invention employs compliant, large area, low cost, flexible piezofilm as the core element of a flexure sensor, attached to any of several different somewhat less flexible or semi-flexible, backbone members of somewhat larger surface area. In some cases, the flexible piezofilm sensor being attached to the less flexible backbone acts to integrate localized strain anomalies and produce an average signal voltage of the flexure to which the combination is exposed. This combination preserves the "soft comfortable" requirement aimed at achieving user compliance, while employing low cost, easy-to-fabricate, sensor methodology.

The sensors of the invention enable a universal body motion biofeedback kit capable of providing the doctor or therapist with an in-office components package from which a suitable biofeedback system can be configured, fitted and adjusted; for a range of different patients, and for a range of different patient problems. The customized system is what the patient wears out of the office. Development of the soft flexible force and motion transducers disclosed herein, were necessary to optimize the universality of the components package or biofeedback kit in the hands of the doctor or physical therapist, to meet all of the objectives of the invention.

Further, it is possible to provide a system for volume application such as for works at Home Depot™, the Marriott™ chain, and the like, or for supermarket employees. These systems would be factory set to baseline statistics for harmful moves or conditions providing warning over a wide range of conditions of the measured variable or variables. These would not need the assistance of a doctor, therapist or trainer. They could be fitted with a fine adjustment control to account for differences in individuals, settings that could be described using base line movements to allow the user to arrive at the proper threshold indication for that reference move.

It was an object of a parent application to provide a mounting appliance system that allows motion sensors to be placed anywhere on the body with a chosen orientation and that is comfortable to wear and non-confining. Many of the athletic training devices on the market are uncomfortable constraining braces that force the user to a particular perdetermined move that may not be correct for every user. The aforesaid mounting appliance system and the transducers and sensors disclosed herein are intended to be companion devices, although either may be used independently with other compatible devices.

An object of this invention is to provide a sensor system that allows abuser to isolate a single folding or twisting motion of the body with a suitable sensor/appliance combination, (e.g. flexing the wrist in a particular plane), so as to provide sensing and instant feedback to cue for proper motion performance and warn against improper motions. It is a related objective to promote a training methodology for such motions, including a "one thing at a time" focus and a natural learning by doing process.

The transducer concepts disclosed herein meet these needs. There are four general transducer configurations within the scope of the invention, all sharing a common dependence on a flexible film sensing element: oval, half oval, trident and compression pad. The oval and half oval lend themselves to mounting in elastic bands such as suspenders, the trident lends itself to mounting at a joint in a wrist, elbow or knee, while the compression pad is optimum for application along the spine. Additionally, introduction of a static overlay switch greatly enhances system capability by introducing one or more absolute levels for the parameter being measured, such as minimum, maximum or optimal, to the sensors of the invention.

An object of this invention is to include in the training system, capability for adjusting the system sensitivity to accommodate different levels of skill, performance, application or severity, in a manner that is simple to set up and adjustment. Many existing training systems for athletic activities compare and force the user to accept a predetermined average motion or range of motion. The transducers disclosed herein have linear output and the range required for optimum parameter adjustability and threshold selection with a suitable control module.

An object of this invention is to provide a limb/body sensing and monitoring system that enables very low cost implementation. Medical systems that help a patient with recovery and rehabilitation, historically, have been expensive and frequently require fitting and ordering of a custom device. The disclosed invention provides a means for in-office configuration and setup of the system so that the patient can leave with a properly fitted custom aid or biofeedback system, and where the fitting "breadboard" and the final device are one and the same, promoting lower costs and reduction in stock requirements.

An object of this invention is to provide training systems easy to wash, clean, or sterilize. These transducers, a preferred example using a Kynar™ flexible piezofilm sensor, are inert to a range of solvents. For example, a common use of Kynar™ film is to line caustic tanks to avoid corrosion. These transducers can be plated, or alternatively deposited with inert elements such as gold, for electroding the transducer film, to preserve environmental inertness.

Further objects and advantages of this invention will become apparent from a consideration of the drawings and ensuing description.

BRIEF DESCRIPTION OF THE FIGURES

FIG. 10 is a perspective view of a wrist appliance with pockets, fitted with a sensor element and backbone structure embodiment of the invention in one pocket.

DESCRIPTION OF THE PREFERRED EMBODIMENT

Figure 1:
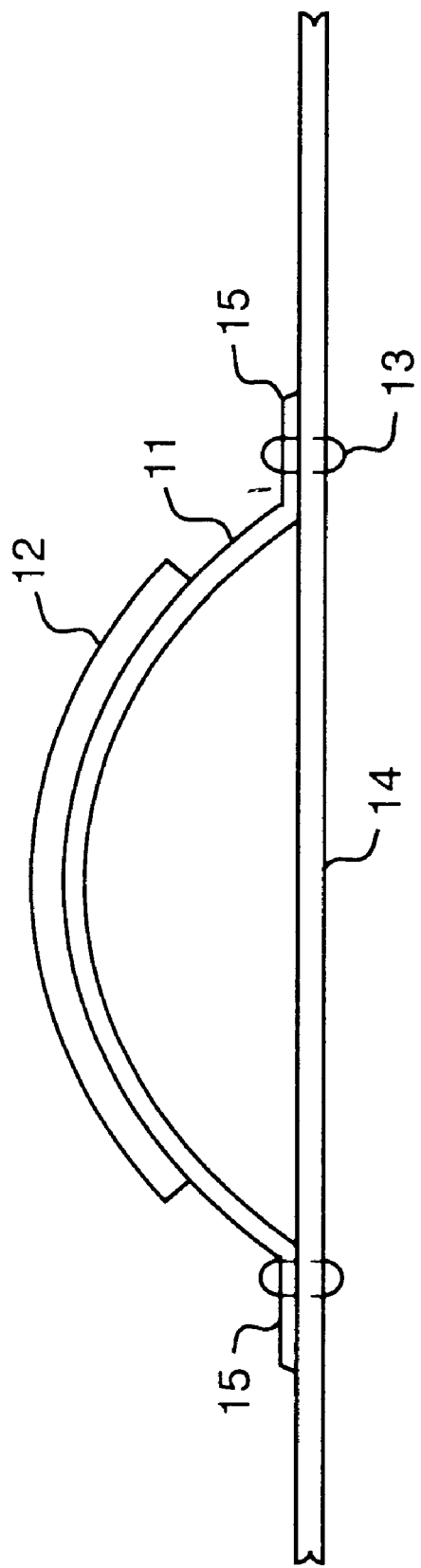
FIG. 1 is a side view of a compliant half oval link sensor embodiment of the invention mounted on a stretchable belt.

The preferred system embodiments described herein utilize a common, self-contained electronic system signal processing and feedback module with a sensitivity adjustment control. The module is mounted or attached to any of the several universal mounting appliances, and is connected electrically, optically, or by wireless means, for data transfer from one or more system sensors. The module generates or triggers a sequence of audible tones or discrete colors from among a limited set of tones or colors, stepwise changing the tones or colors within the set in response to real time variations in sensor input, from which the incremental range of motion is easily interpreted. Other forms of multi-step annunciation are within the scope of the body motion monitoring systems with which the claimed sensor systems are compatible. The module described above, and other embodiments of the module providing the same or similar functionality, can be characterized as a body motion monitoring and multi-step annunciator system.

In the general case, an appliance set is selected for the appropriate the body joint of interest. The placement and orientation of a sensor on or within the appliance is guided by a coded scheme of markings or pockets, selectable depending on the motion of interest and easily identified in instructions for repeatability. The feedback module is connected to the sensor and mounted to the appliance. The sensor invention disclosed and claimed herein is based on a key sensor element, a flexible piezofilm, such as Kynar™, with inert metal electroding, integrated with a very compliant, larger area host member or backbone, as a linear, large signal sensing element. The a larger area semi-flexible backbone and sensor in combination act to integrate localized strain anomalies and produce an average signal voltage of the distortion affecting the sensor assembly. As one pushes to design with softer and larger support elements, local buckling or deformation becomes more likely. The large area integration of strain of the configurations disclosed herein, allow these obstacles to be minimized and overcome. The flexible film sensor/backbone combination can take the form of several shapes including; oval or circular, half oval, trident and compression pad.

The disclosed sensor systems are mechanically soft, high compliance, elements that can measure motions over extended ranges and perform satisfactorily where developed forces may be very low. A variety of mounting appliances and methods are disclosed, that together provide a one-to-one figment capability for one or more of the various motion-related positions on the body. In other words, there is a preferred appliance and piezofilm transducer configuration for each of the back, wrist, knee, and so on. Each appliance is universal in that it provides coded location or anchor points and orientations for mounting the sensor for the intended application. The coded location or anchor points facilitate a close description of the figment and promote easy repeatability from written or verbal instructions. The flexible film transducer can be configured to be compatible with each mounting need.

For well defined applications such as for replacing lifting support belts worn by employees of Home Depot™, the Marriott™ chain and others, factory preset units calibrated to population statistics can be used. These can have fine tune adjustment controls that can be adjusted to a reference motion or shock The doctor, therapist, or user fits the system to a particular need by selecting planes of motion at the joint of interest via a sensor mounting point and orientation, and choosing a flexible film transducer configuration that meets the range of motion using the sensitivity adjustment. It is important to recognize that the human and animal joint motion can be more than a simple folding of a joint on a fixed hinge line. The flexible film transducer/appliance combination is able to integrate more complex motions that include a twisting or rotational component, or omni-directional flexure as over a point on the backbone. As the user, when properly fitted, moves through the normal range of motion, a sequence of audible tones from a limited set of tones is generated by the system, providing instant feedback proportional the sensed amount of flexure, with easily interpreted resolution. Alternate and addition forms of feedback may include colored lights, displays, vibration, and so forth. Position and motion data can also be transmitted between sensors or to a ground station data logger or to any other remote display.

Figure 6:
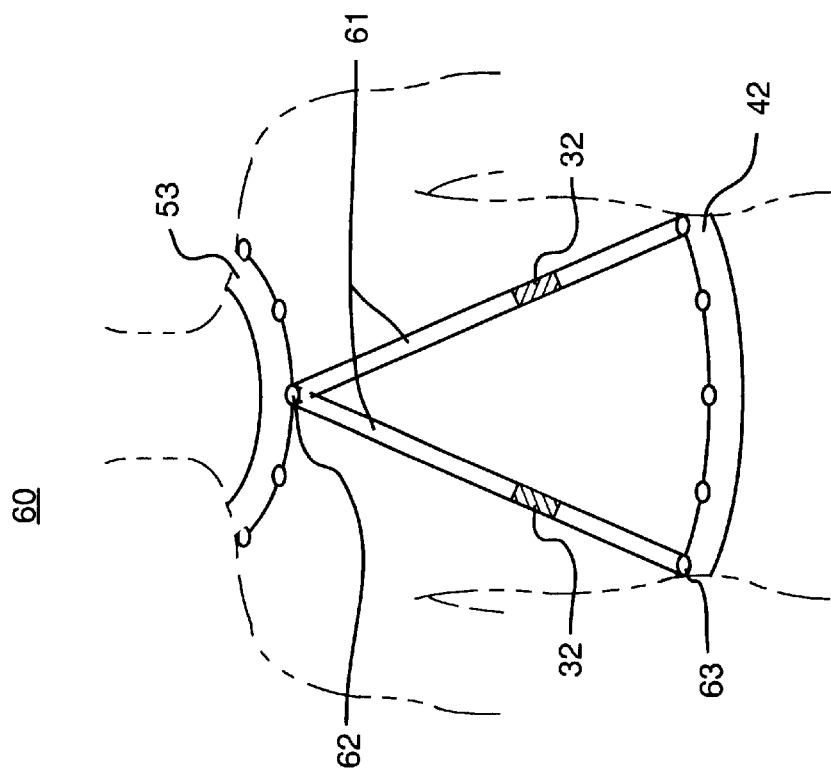
FIG. 6 is a back view of a person fitted with a belt and collar, each with multiple anchor points, and two connecting suspenders, each incorporating sensors of the invention.

Referring now to FIG. 6, there is disclosed a preferred biofeedback system embodiment of the invention suitable for monitoring the back and torso for twisting, windup, rolling, and hunching motions. Suspender system 60 includes suspenders 61, which are attached between collar 53 and belt 42, at selected anchor points 62 and 63. Suspenders 61 are configured with respective sensor elements 32, connected mechanically in series to carry the load of the suspenders in tension. Sensor elements 32 are electrically connected to the biofeedback module 143 of FIGS. 14 and 15, (not shown in FIG. 6), which in use can be mounted to belt 42 or elsewhere on the user. Sensor elements 32 may be specified to be sensors of the invention such as compliant oval sensor 20 of FIG. 2, or a conventional sensor such as a potentiometer, encoder or switch. Alternate configurations for this appliance system are shown in FIGS. 3, 4, 5 and 7.

Figure 5:
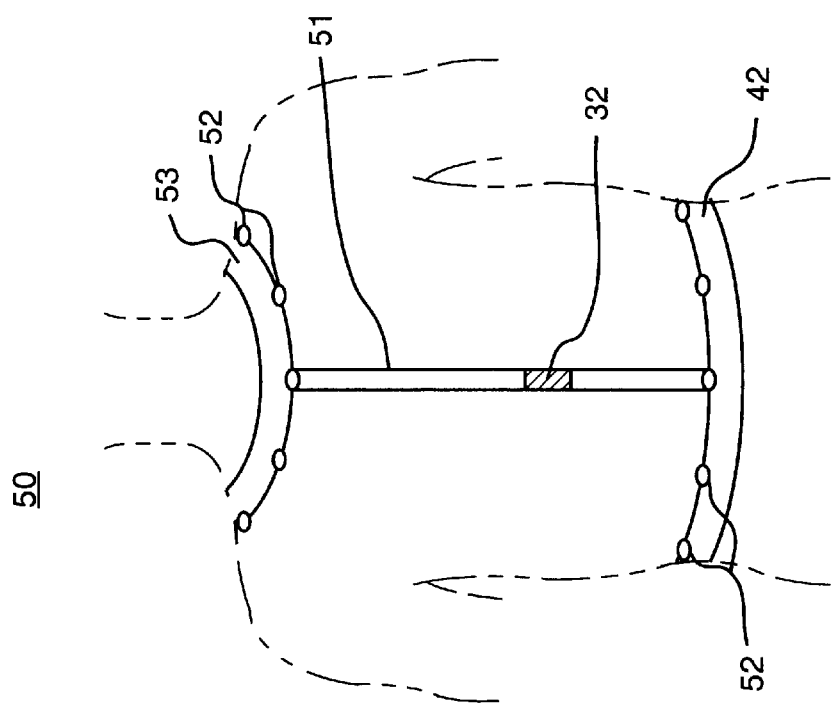
FIG. 5 is a back view of a person fitted with a belt and collar, each with multiple anchor points, and a connecting single vertical suspender incorporating a sensor of the invention.
Figure 16:
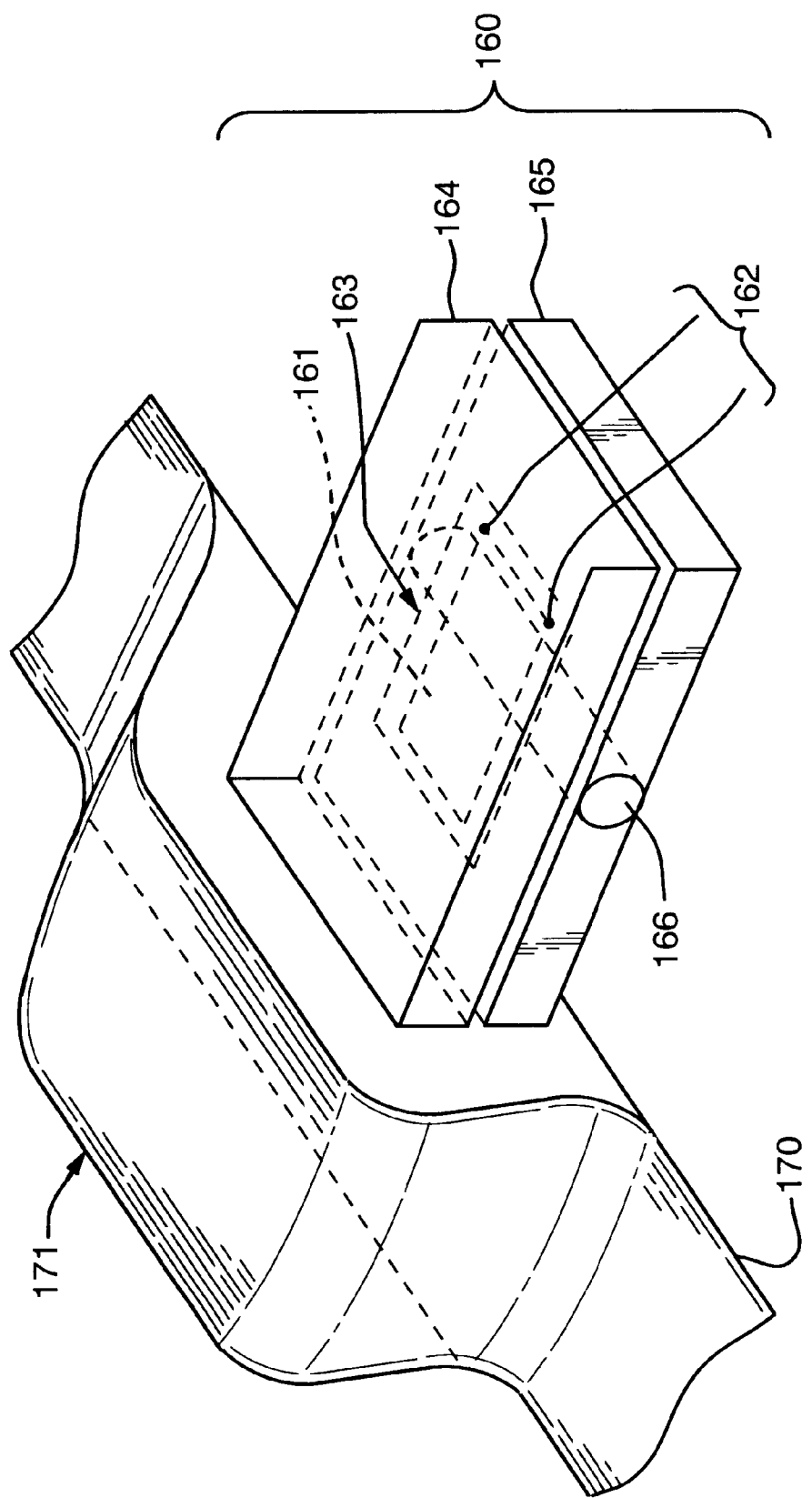
FIG. 16 is a transparent, perspective, partial view of a strap appliance and a compression pad transducer embodiment with a thin film sensor element laminated between two compressive pads, the underside pad having a higher density fulcrum section over which the sensor element is flexed.
Figure 17:
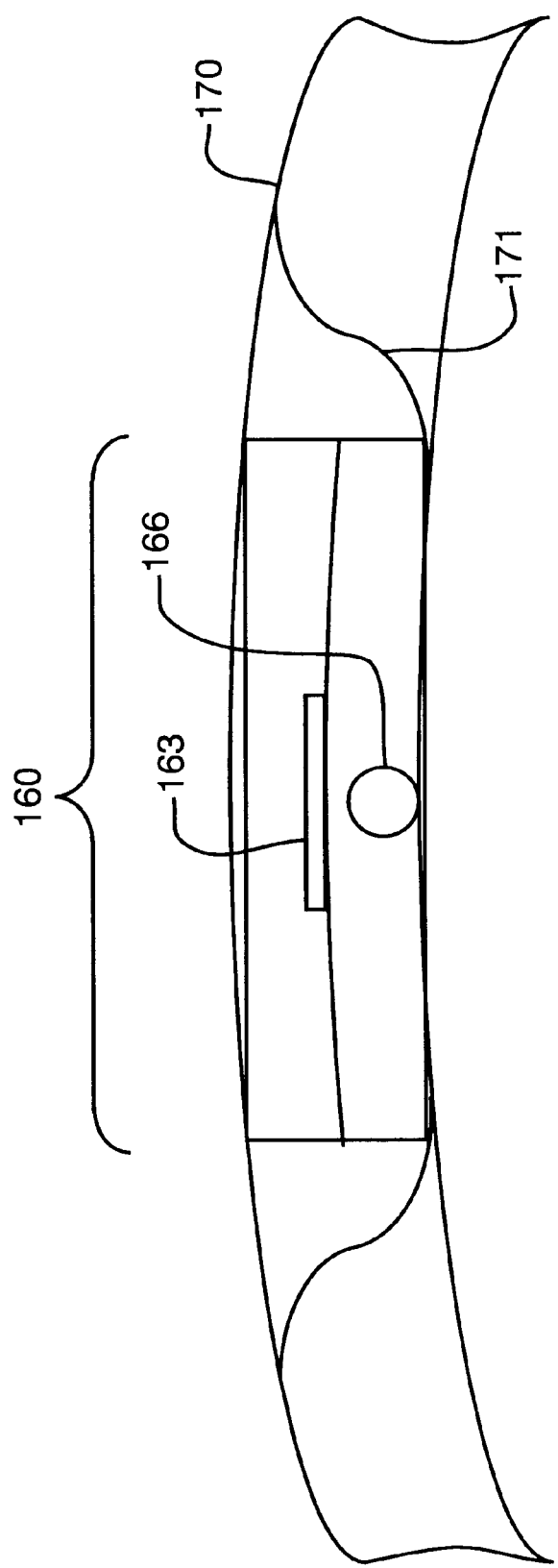
FIG. 17 is a partial cross section of a strap appliance and a compression pad transducer embodiment with the fulcrum section oriented perpendicular to the belt line.

As another preferred embodiment for back motion, the sensor shown in FIGS. 5 and 6 can take the form of a sponge-like compression pad with a planar, flexible film-sensing element laminated or embedded within the pad, such as the compression pad sensor 160 of FIG. 16, or 170 of FIG. 17. The advantage of this sensor configuration is that it performs the motion measurement uniformly for a range and variety of spine configurations.

Referring now to FIG. 10, there is disclosed a preferred biofeedback system embodiment of the invention for monitoring the motion of limb joints, including the elbow, wrist, ankle and knee. Wrist joint monitoring system 100 includes wrist appliance 102 with coded mounting pockets 101, flexure sensor 93 mounted on shaped backbone 105, with signal leads 94 connecting to a signal processing and feedback module such as module 143 of FIG. 14 (not shown in FIG. 10). In practice, the biofeedback module is typically attached to wrist appliance 102 in the manner illustrated in FIG. 14.

Figure 3:
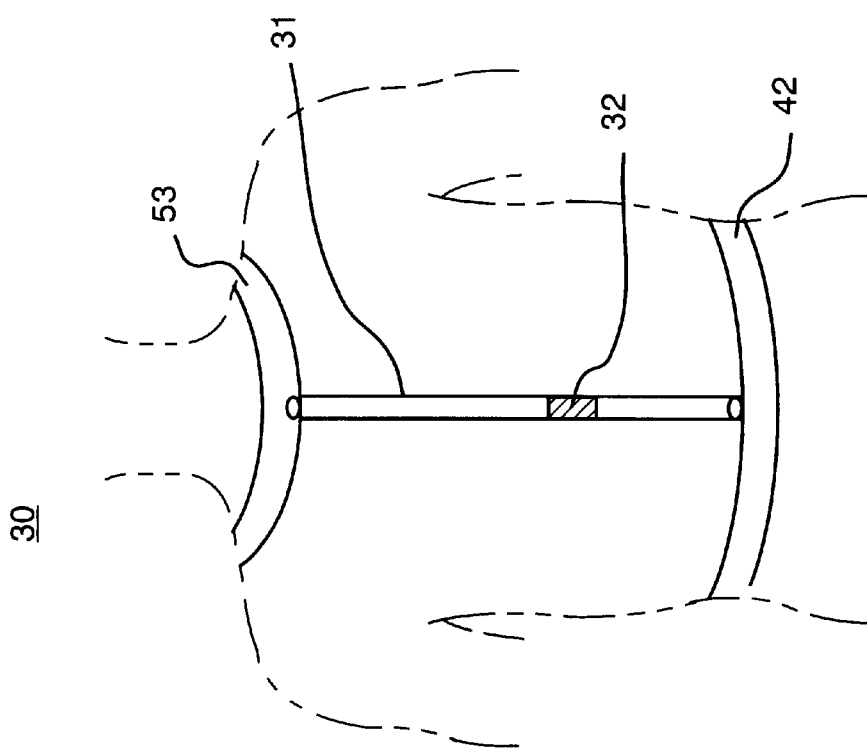
FIG. 3 is a back view of a person fitted with a belt and collar, with a connecting single vertical suspender with a sensor of the invention aligned over the spine.

Referring generally to FIGS. 3, 4, 5, 6, and 7, suspender style mounting appliances are disclosed, suitable for use with the oval, half oval, or compression pad sensors of the invention for measuring various motions of the back and spinal column. Referring to FIG. 3, suspender system 30 consists of waist belt 42, collar 53, and connecting vertical suspender 31 configured so as to be aligned with the user's spinal column. Suspender 31 is constructed of an elastic material so as to stretch in compliance with the user's motion without noticeable effort. Low force, large elongation sensor 32 is attachable to suspender 31 so as to be placed in tension in proportion to the linear extension of the suspender length.

Figure 4:
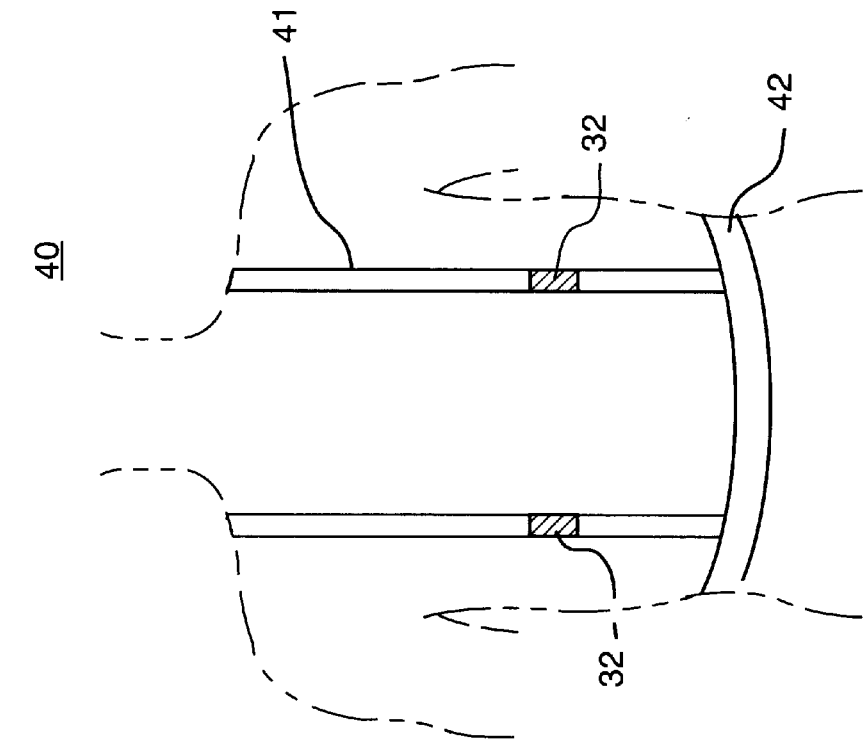
FIG. 4 is a back view of a person fitted with a belt with two vertical suspenders extending up over the shoulders, incorporating sensors of the invention.

Referring to FIG. 4, suspender system 40 includes belt 42 to which is attached a pair of over the shoulder suspenders 41. Suspenders 41 are constructed of an elastic material so as to stretch in compliance with the user's motion without noticeable drag or resistance. Low force, large elongation sensors 32 are attachable to suspenders 41, the outputs connectable as a sum or difference to a biofeedback module of the invention, to detect tilting or lifting of one or both shoulders.

Referring to FIG. 5, suspender system 50 includes belt 42, which is configured with multiple attach points 52 arranged at uniform intervals along its length. Collar 53 is similarly equipped with attach points 52. Suspender 51 is adjustable, stretchable, and connectable at any combination of belt and collar attach points to be aligned and compliant with the motion of interest. A low force, large elongation sensor 32 is applied to suspender 51 and connected to a biofeedback module of the invention in the manner described above. Suspender 51 is illustrated here in the over-the-spine, vertical position.

Referring to FIG. 6, suspender system 60 includes compliant suspenders 61, configured with respective low force, large elongation sensors 32, arranged in an inverted V form and attached at selected anchor points 62 and 63 between collar 53 and belt 42. Anchor points 62 and 63 are three of a multitude of selectable anchor points arranged at uniform intervals along the length of the belt and collar, each point coded so as to be easily designated in instructions or reports. As in previous embodiments, the sensors are electrically connected to a biofeedback module.

It will be apparent from the embodiments of FIGS. 5 and 6 that by choosing the appropriate anchor points and suspender elements, different motions of the back such as rolling, hunching, and twisting, can be selectively favored. The oval, half oval and compression pad transducer configurations of the invention were optimized for these mounting methods.

Figure 7:
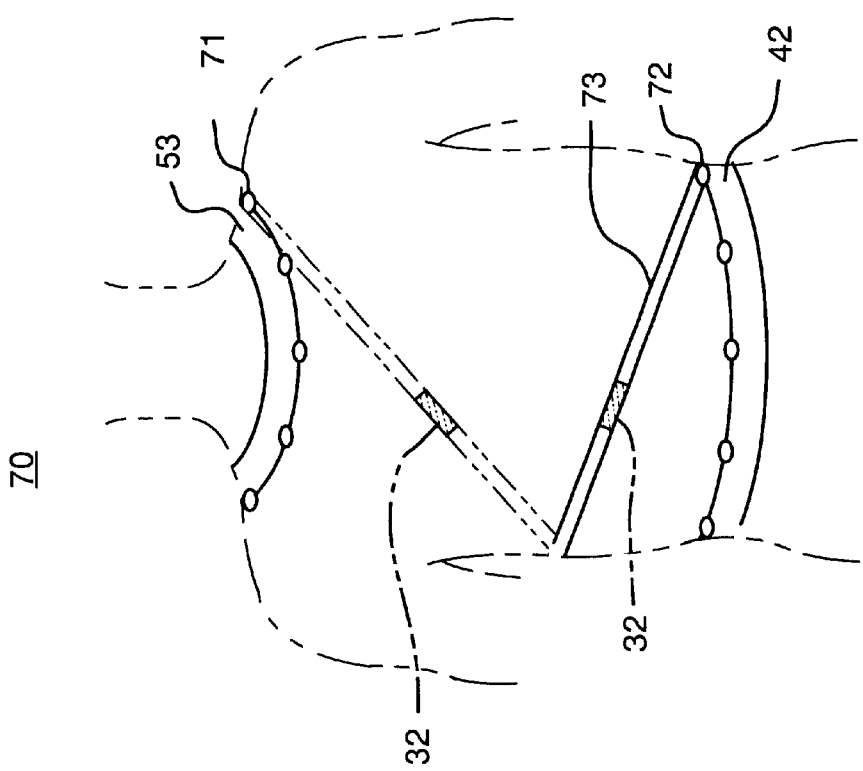
FIG. 7 is a back view of a person fitted with a belt and collar, each with multiple anchor points, and a connecting single suspender incorporating two sensors of the invention, the suspender configured in a diagonal, wrap-around back of belt to front of collar arrangement with one sensor in front and one sensor in back.

Referring to FIG. 7, suspender system 70 illustrates a variation on the systems of FIGS. 5 and 6, suspender 73 with sensor 32 being configured and attached to anchor points 71 and 72 on collar 53 and belt 42 so as to wrap around the torso of the user.

Figure 11:
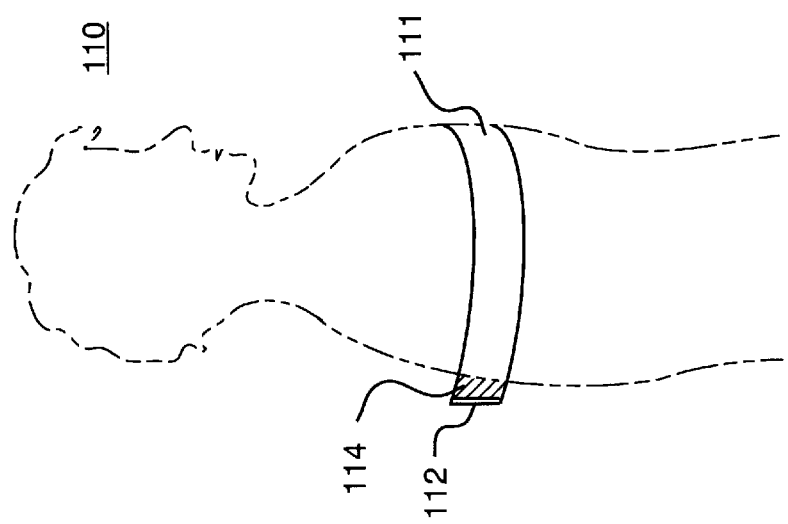
FIG. 11 is a side view of a person fitted with a chest belt appliance and back-mounted, flexible piezofilm-based, compression pad embodiment of the invention.

Referring to FIG. 11, back roll belt system 110 includes a belt 111 sized and intended to be mounted chest high on the user, to which the flexible, compression pad sensor 112 can be installed in pocket 114, so that sensor 112 is placed between belt 111 and the body. The sensor and operation of back roll belt system 110 is further described below.

Figure 13:
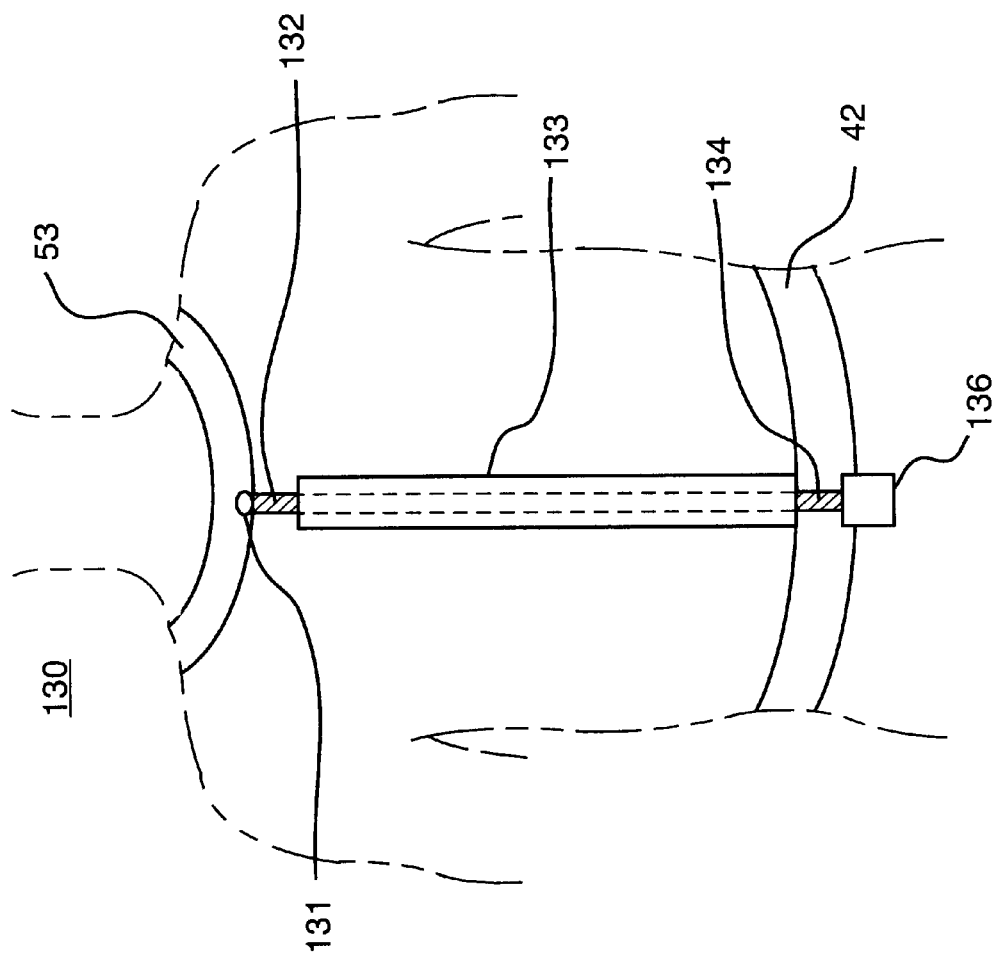
FIG. 13 is a backside view of a person fitted with a belt and collar appliance, with a belt mounted rotary sensor base element and a connecting spinal suspender with sensor rod element, with which sensors of the invention may be combined to provide more complex monitoring and feedback information.

Referring to FIG. 13, there is disclosed a back motion monitoring system 130, which includes belt 42 and collar 53 of previous embodiments, worn with anchor points aligned over the spine. The sensors and operation of back motion monitoring system 130 are further described below.

Figure 9:
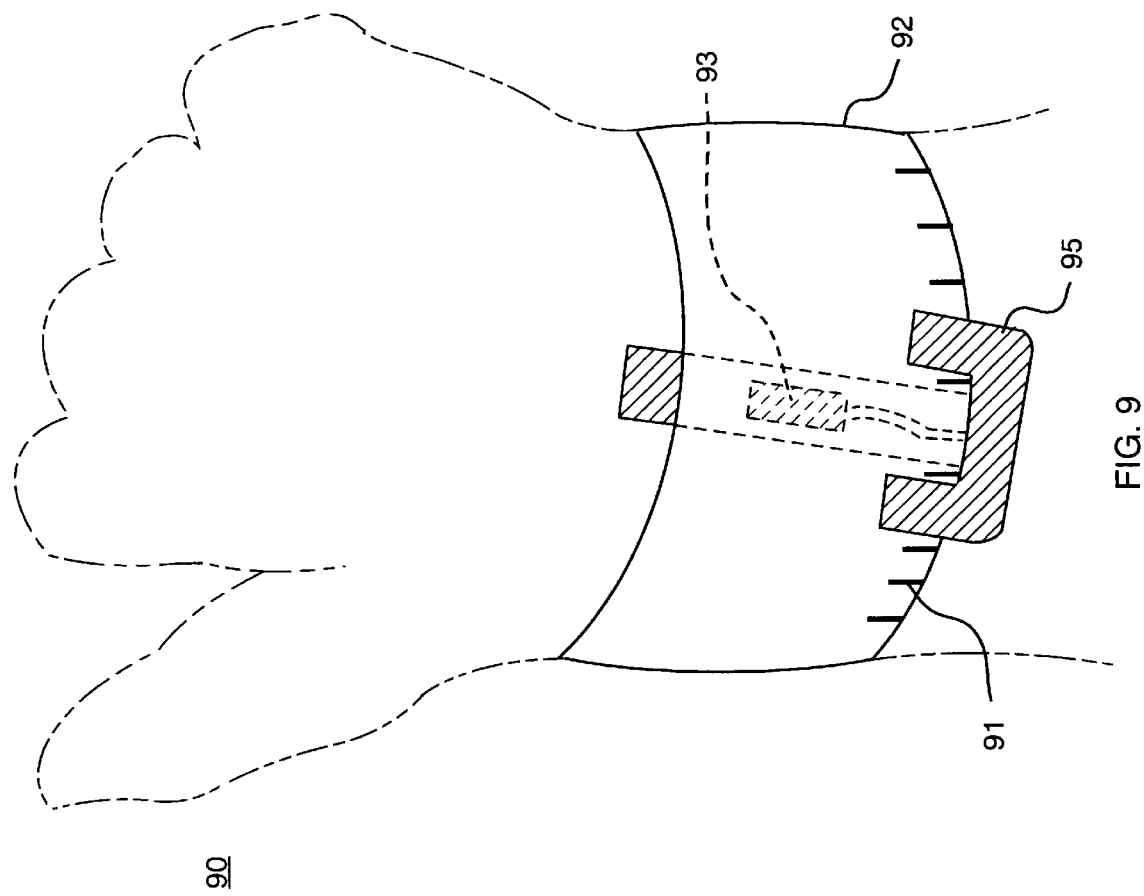
FIG. 9 is a perspective view of a wrist appliance fitted with a sensor element and trident backbone embodiment of the invention.
Figure 14:
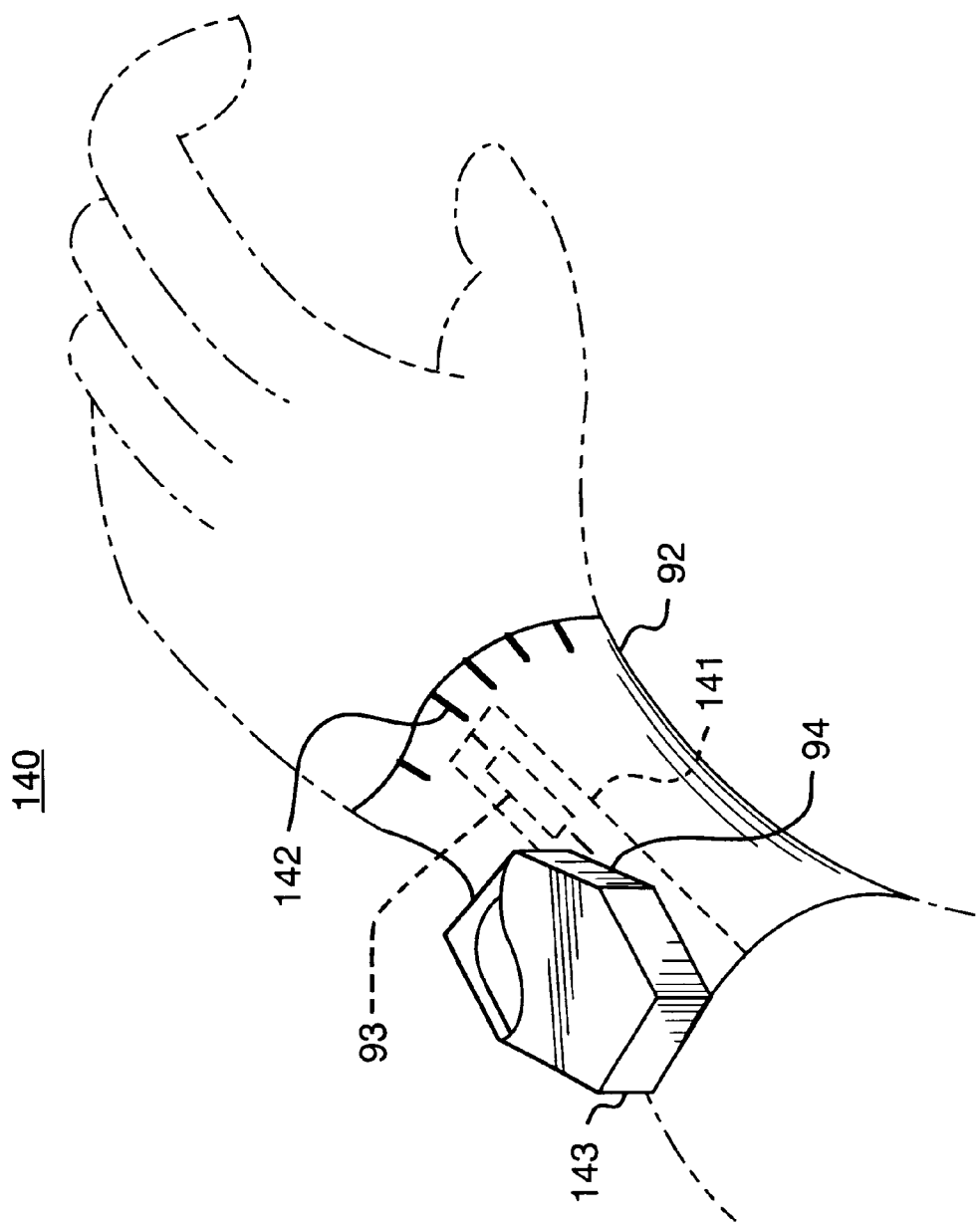
FIG. 14 is a perspective view of a wrist mounted appliance with sensor pocket and index marks, with a trident shaped flexure sensor embodiment of the invention mounted in the pocket and connected to a biofeedback module attached to the wrist appliance.

Referring to FIGS. 9, 10 and 14, there are disclosed wrist appliances that incorporate mounting options and coding for selection and placement of sensors. Wrist appliance system 90 of FIG. 9 has coding marks 91, spaced along the edge of wrist band 92, with which flexible film sensor 93, affixed to trident backbone 95, can be selectively aligned. Signal leads 94 extend from sensor 93 for connection to a biofeedback system module, which may be attached directly to the wrist band appliance. Wrist appliance system 100 of FIG. 10 has coded. pockets 101 on wrist band 102, into which flexible film sensor 93 mounted on backbone 105 may be selectively fitted. Again, signal leads 94 are connectible to a biofeedback system module.

Similar to FIGS. 9 and 10, wrist appliance system 140 of FIG. 14 includes a wrist band 92, configured with pocket 141 and coding marks 142. Biofeedback module 143 is attached by a clip to the wrist appliance and connected by leads 94 to sensor 93 in pocket 141.

Knee and ankle appliances of the invention closely correspond in construct and use to the appliances of FIGS. 9, 10 and 14, with mounting and coding features consistent with the details described above. Here the trident configuration consisting of the Kynar film-sensing element mounted on a backbone structure is optimum.

There are four distinct embodiments of the sensor invention claimed herein, which in combination with the appliances, can accommodate the various requirements of the biofeedback system. In particular, the sensors are characterized as low force, high elongation devices; and in combination with the appliances, provide the capability to be adapted to unique mounting requirements and coded for repetitive placement. The four embodiments include the oval, half oval, trident and compression pad transducers described.

Referring to FIG. 1, half oval sensor system 10 is a compliant half oval link transducer consisting of half oval link 1, attached to flexible band 14 by fasteners 13, with a single flexible piezofilm sensor element 12 affixed to half oval link 11. Half oval sensor system 10 has springlike response to tension applied at its end points, gradually straightening link 11 under increasing tension and recoiling to restore link 11 to its original shape when the tension is released. Link 11 may be a plastic (such as Mylar) or metal member formed in the shape of a half oval, with attachment tabs 15 extending from each end. Other means of attachment of link 11 to band 14 are within the scope of the invention.

The compliant oval transducer consists of a circular or oval shaped backbone member upon which large area flexible piezofilm sensors are mounted. When more than one sensor is used a first pair is mounted with the two sensors on opposite sides of the backbone member, at either the axis of compression or the axis of elongation, connected in series and positioned diametrically opposite so as to be additive when the oval is deformed by the companion mounting appliance. A second pair of sensors can be added, displaced 90 degrees from the first pair. The alternative pairs of sensors see opposite polarity of signal and are connected accordingly to provide an additive signal upon deformation of the oval. The oval mounted sensor/backbone assembly is then fitted into a mounting appliance such as an elastic suspender leg that captures the assembly. Electrical leads are dressed from the sensors to a transmitter or to a local signal processing and feedback device. As tension or compression is applied to the transducer, the oval deforms proportionately producing a signal level corresponding to the amount of tension in the appliance produced by body motion.

Figure 2A:
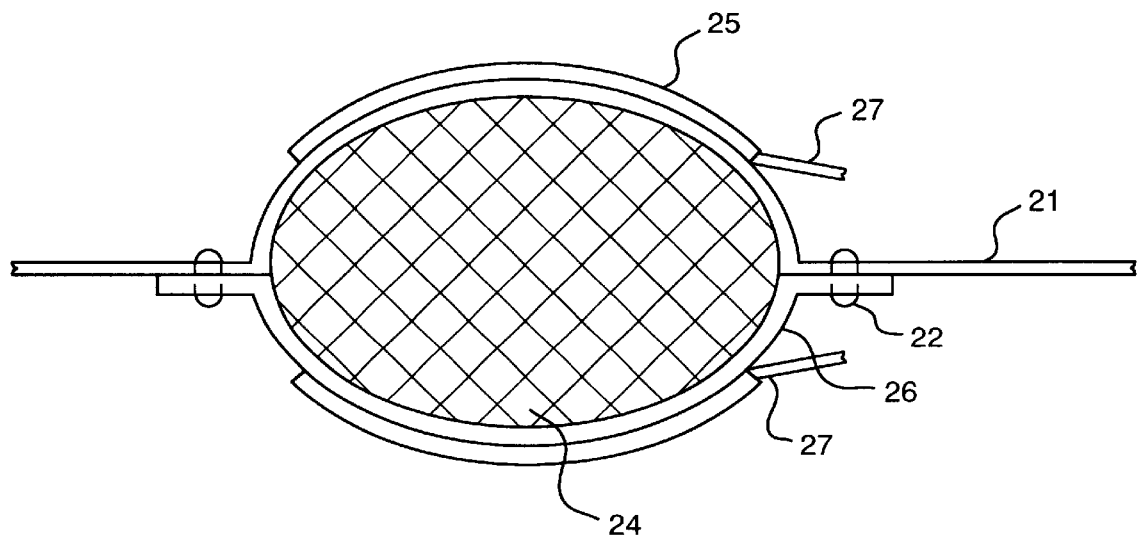
FIG. 2A is a cross section view of a compliant oval sensor embodiment mounted in tension between two belt sections.

Referring to FIG. 2A, oval sensor system 20 is a compliant oval transducer consisting of a flexible band 21 with a second flexible band 26 attached to it by fasteners 22 around compliant oval member 24. Oval member 24 is formed from a sponge-like compressible material that deforms readily under increasing band tension or lateral compression to an elongated form, but expands to its origin shape when the tension or lateral compression is released. Flexible film flexure sensors 25 are affixed to bands 21 and 26 on each side of the oval; each having individual signal leads 27. The respective leads can be wired individually or connected in aiding or opposing polarity to serve processing objectives in related multi-sensor configurations, into a signal processing and feedback module.

Figure 2B:
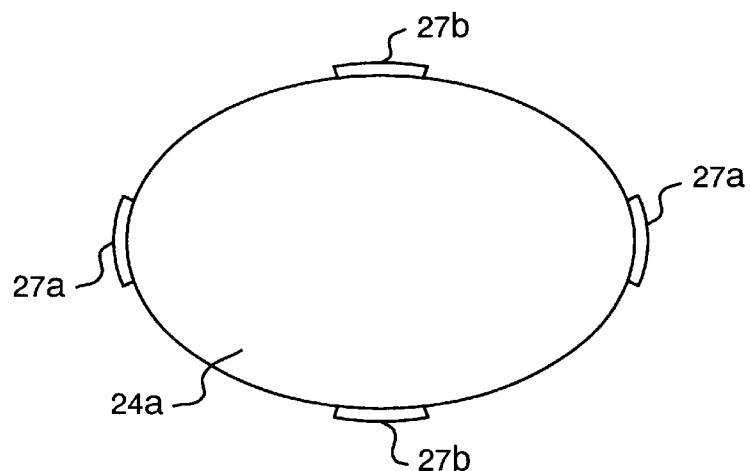
FIG. 2B is a cross section view of a compliant oval sensor embodiment with opposing end leads and opposing side leads embedded into the conductive mass of the sensor.

Referring now to FIG. 2B, a further embodiment of the oval sensor of FIG. 2A has a compliant oval base member 24A that performs as a semi-flexible backbone for a first pair of piezofilm sensors 27A emplaced on opposing ends of the elongation axis, and a second pair of piezofilm sensors 27B emplaced on opposing ends of the compression axis. This sensor system, consisting of the flexible oval or circular shaped Mylar backbone member 24A, with the flexible piezofilm sensors bonded to it, creates a self generated voltage proportional to the change in pressure, or tension on the oval base member. It will be readily apparent to those skilled in the art that the output of sensors 27B can be added together, but will be of opposite polarity as the output of sensors 27A, which can also be added together, so that the sum of the 27B sensors less the sum of the 27A sensors provides potentially greater resolution as to the deformation of base member 24A when it is employed directly as the core element of a compliant oval sensor system similar in utility and application to sensor system 20 of FIG. 2A.

Suitable electronics and audio or signal output capability, and even a battery, may be embedded in the oval base member of transducer 24A, or otherwise integrated or incorporated into localized sensor support circuitry, resulting in a fully self-contained sensor/biofeedback device that in combination with the appropriate appliance, functions in the manner of the biofeedback systems described.

Referring to FIGS. 8, 9, 10 and 14, as has been disclosed in earlier applications by this applicant, the flexure sensors illustrated consist of a strain gage-instrumented beam or backbone, utilizing a flexible piezofilm sensor for measuring flexure over a relatively large surface area. In the current embodiments, flexible piezofilm (such as Kynar) is used and the sensing area is approximately 0.4 by 1 inch. The area measured can be extended by increasing the beam dimension, the sensing dimension or both. It is also possible to instrument the beam with other variable resistance elements, magnetic systems and the like, all within the scope of the invention although all are deemed less effective toward meeting the objectives of this invention.

The bending beam or backbone of the various sensor assemblies of the invention can take the form of a simple rectangle, coded and sized to fit into the pockets of the various appliances of the invention. Alternatively, a trident form of sensor backbone, as illustrated in FIG. 9, provides a convenient form factor for figment to some belt-like appliances. The trident has the structural feature for providing outer legs that pass over a mounting belt, pocket, or the like, to position and hold the sensing element in the proper location.

Figure 8:
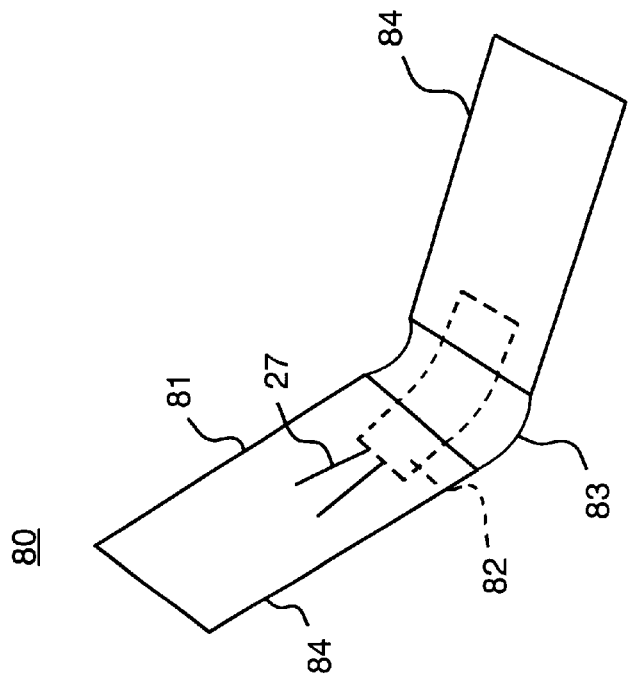
FIG. 8 is a perspective view of a hinge motion sensor element and base assembly embodiment, optimized for joint monitoring.

Referring to FIG. 8, to enable the hinge-like action of hinge sensor system 80, sensor element 82 is mounted on backbone 81, and has leads 27 connectable to a biofeedback module of the invention. Backbone 81 is pre-configured for compliant bending at its central zone 83, with stiffer end zones 84 that are secured to the respective members of the joint of interest.

The flexible mounting appliances and methodology of the invention are also adaptable to accommodate conventional sensor elements such as strain gages, switches, potentiometers, and encoders. However, the sensors disclosed herein significantly enhance the functionality and help meet overall objectives of low cost implementation, comfortable to wear and easily sanitized components. Rotary potentiometers and encoders are desirable sensors for integration within certain system configurations to measure rotation or twisting of the back or wrist, as for variants of the several embodiments disclosed in the figures.

Referring again to FIG. 11, back roll belt system 110 is a more specific implementation of the invention for measuring rolling of the back such as in lifting a weight from the floor. Sensor 112 may be the compliant oval sensor system 20 of FIG. 2, or the compliant oval sensor 24A of FIG. 2A. The compliant characteristic of the sensor installation acts to integrate out the "noise" component of the motion or flexure signal that results from irregularities in the spine or in the placement of the sensor on the spine, making the location and orientation of the appliance and sensor less critical. The output of the sensor is connected to a biofeedback module of the invention.

Referring to FIGS. 16 and 17, there is illustrated a compression pad sensor 160 and mounting belt 170 combination for application such as to the user's back. Mounting belt 170 has a sensor pocket 171, within which compression pad 160 can be installed, and can be strapped to the user so as to position the sensor over the user's backbone. Compression pad 160 consists of a piezofilm element 161 with electrical signal leads 162, mounted on a backing substrate 163; this assembly encased between a top compliant pressure pad 164 and bottom compliant pressure pad 165 so as to form the compliant pad sensor. Bottom pad 165 is configured to include a fulcrum element 166, which can be a discrete structural foam member of higher density than pad 165, or a specific region of pad 165 where the density or "hardness" of the pad has been altered so as to provide a fulcrum or ridge across which piezofilm element 161 and substrate 163 can be flexed.

As contrasted by FIG. 16 and FIG. 17, compression pad sensor 160 can be configured internally or by orientation of installation in pocket 171 of mounting belt 170 to have the fulcrum element 166 arranged in line or perpendicular with the belt line, depending on which way the desired body flexure is best detected.

Referring to FIG. 13, there is disclosed a back motion monitoring system 130 configured for isolating and measuring twisting motions of the back. The system includes belt 42 and collar 53 of previous embodiments, worn with anchor points aligned over the spine. An absolute position sensing rotary switch 136, which may be an encoder or potentiometer, the stator of which is attached to belt 42. Motion transfer strut 132 extends from the rotor of rotary switch 136 to collar 53 at anchor point 131, and is encased in a guiding shroud 133. Rotary motion is transferred between the upper body as referenced by collar 53 and the lower body as referenced by belt 42 to absolute position sensing rotary switch 136, and hence to a biofeedback module of the invention. This setup can be further configured with additional straps and sensors of the invention as described herein, for more complex monitoring schemes.

An alternate configuration of the back motion monitoring system of FIG. 13 for monitoring linear contraction and extensions of back bending, incorporates a static overlay capability that provides one or more absolute position references which can be used to reset an integrator or zero out drift in a dynamic measurement systems such as the compliant oval sensor system of FIG. 2A. Referring again to FIG. 13, but in the context of a static overlay device, the body of switch 136 is connected to belt 42. One end of motion transfer strut 132 is connected to collar 53 at anchor point 131, and the other end is slideably connected to switch 136 so that the switch is actuated when the transfer strut reaches the predetermined reference position. Shroud 133 restricts and protects transfer strut 132 from bucking under compression as in an auto throttle cable assembly. In some cases, it may be useful to incorporate more than one switch closure reference position; one switch incorporating more than one position such as an upper and lower limit, or by using more than one switch.

Piezofilm sensors offer the best fit for meeting the objectives of this invention, however there are disadvantages to the piezofilm sensors; they do not have a static or d.c. response. While the low frequency response can be very low, 0.01 hz or less, practical considerations move this lower limit to the 0.1–0.3 hz range. Two mechanisms 1) dynamic compensation and 2) a static overlay system, overcome this disadvantage, and can be combined with the measuring systems to significantly improve performance.

The inherent, non-zero low frequency cutoff in piezofilms will distort the magnitude and phase of the signal. However, it is a known and calculable amount which can be compensated for by analog signal processing or by numerical means within signal processing and feedback module 143 of FIG. 14. However the static overlay system 130 of FIG. 13 offers a significant alternative.

It is common practice to use signal and or integrator reset circuits to yield quasi-static or quasi-d.c. response. When a system is not capable of zero frequency response, drift and signal lag occur. Integration of offsets and a.c. coupling and non static sensors preclude true static (zero frequency) response. Reset switches are commonly used to establish a new absolute reference at a point(s) in time or position.

Note that the static reset system shown in FIG. 13 can be used alone to provide a single point of reference. Also, the switch can replaced by a linear potentiometer or a linear encoder (indexed incremental or quadrature) to function as an absolute analog system over a limited range. It is however, very effective as a low cost static overlay that is used with one of the dynamic systems disclosed in the other figures. When these systems are combined there is good synergy. The dynamic system provides necessary refinements of signals for early warnings to be sounded so that an improper lift is aborted or a range of motion is not exceeded. The static overlay capability reinserts a static reference and can be used to provide an absolute limit. While a dynamic sensing system with static zero frequency response could be used, the combined non-zero response sub-system in concert with the static overlay sub-system is a much better choice for the system inventions disclosed herein.

Figure 12:
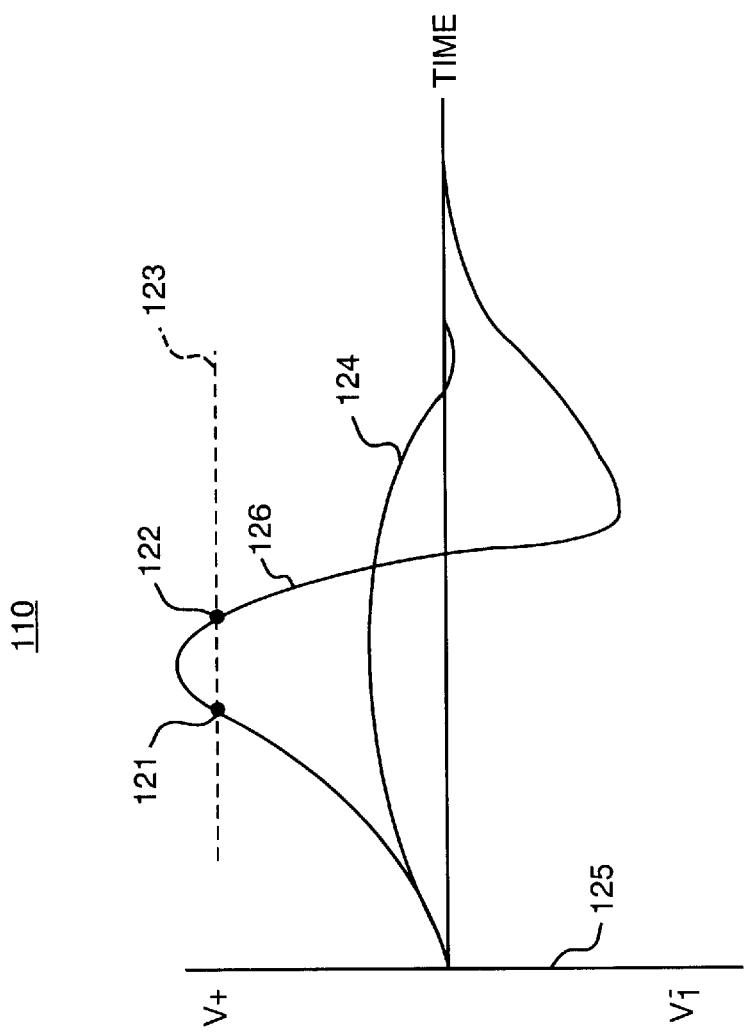
FIG. 12 is a graph of a two element sensor signal as voltage over time.

Referring now to FIG. 12, there is disclosed a model graph demonstrating some of the signal characteristics used by the biofeedback module electronics to improve the measurement discrimination, quality and applicability of the thin film flexure sensor inputs. Voltage versus time curves are illustrated for lifting signal 126 and arm position signal 124. In the simplest case a peak motion threshold 123 is applied to lifting signal 126, sounding a warning that an improper lift is about to be performed. Further discrimination can be had by comparing the length of time that lifting signal 126 is above threshold 123 by examining the time between points 121 and 122 of the signal, making a decision only if the signal is above the threshold 123 for the correct range of time. This type of signal processing can inhibit the incidents of false alarms.

Referring again to FIG. 12, there is disclosed a model graph demonstrating some further uses of signal conditioning to improve the discrimination of the instrument or to avoid false warnings. An important characteristic of the lifting signal 126 such as achieving a given threshold may be combined with a second signal such as the position of the arms relative to the waist 124 where both a required threshold of the lifting signal and a required minimum position of the arms above the waist would be required simultaneously, to trigger a warning signal.

The simplest embodiment of the full system uses instant, audible feedback. The feedback is in the form of stepped tone pitches that correspond one-to-one with selected or programmed signal thresholds. In noise sensitive or noise saturated environments where audio feedback is either distracting or ineffective, the same general functionality can also be accomplished by using discrete colors that correspond one-to-one with selected or programmed signal thresholds. The tone or discrete color that corresponds to the greatest motion threshold reached is held for a fraction of a second (0.1 to 0.5 seconds). When using color feedback, the color level corresponding to the highest input signal can be flashed for further emphasis, analogous to the holding of the peak tone. The effect of holding the peak motion signal is to improve the likelihood that it will register with the user as a meaningful measure of his or her effort.

The signal spacing between thresholds can be linear or non-linear so that early warning, or degrees of warning, can be achieved when an undesired body movement is occurring. It can be in bands so that training can be aimed at a central point. The feedback can take any other usable form either separately or in parallel with the audible feedback.

The information collected by the system can also be transmitted to a data logger or ground based computerized data collection system for post analysis and for establishing norms and correlating motion histories with future injury or other physical problems. Statistical data collection can be performed as a histogram of threshold events.

The biofeedback system preferably uses five tones or colors, however more or fewer are possible, the resolution of the collected data corresponds to the number of thresholds and feedback tones. The Applicant's research indicates that a methodology using a relatively few discrete tone steps or colors is significantly easier for the average person to detect, resolve and remember on a real time basis, than are continuously varying or many incrementally small step changes in frequency or amplitude.

Figure 15:
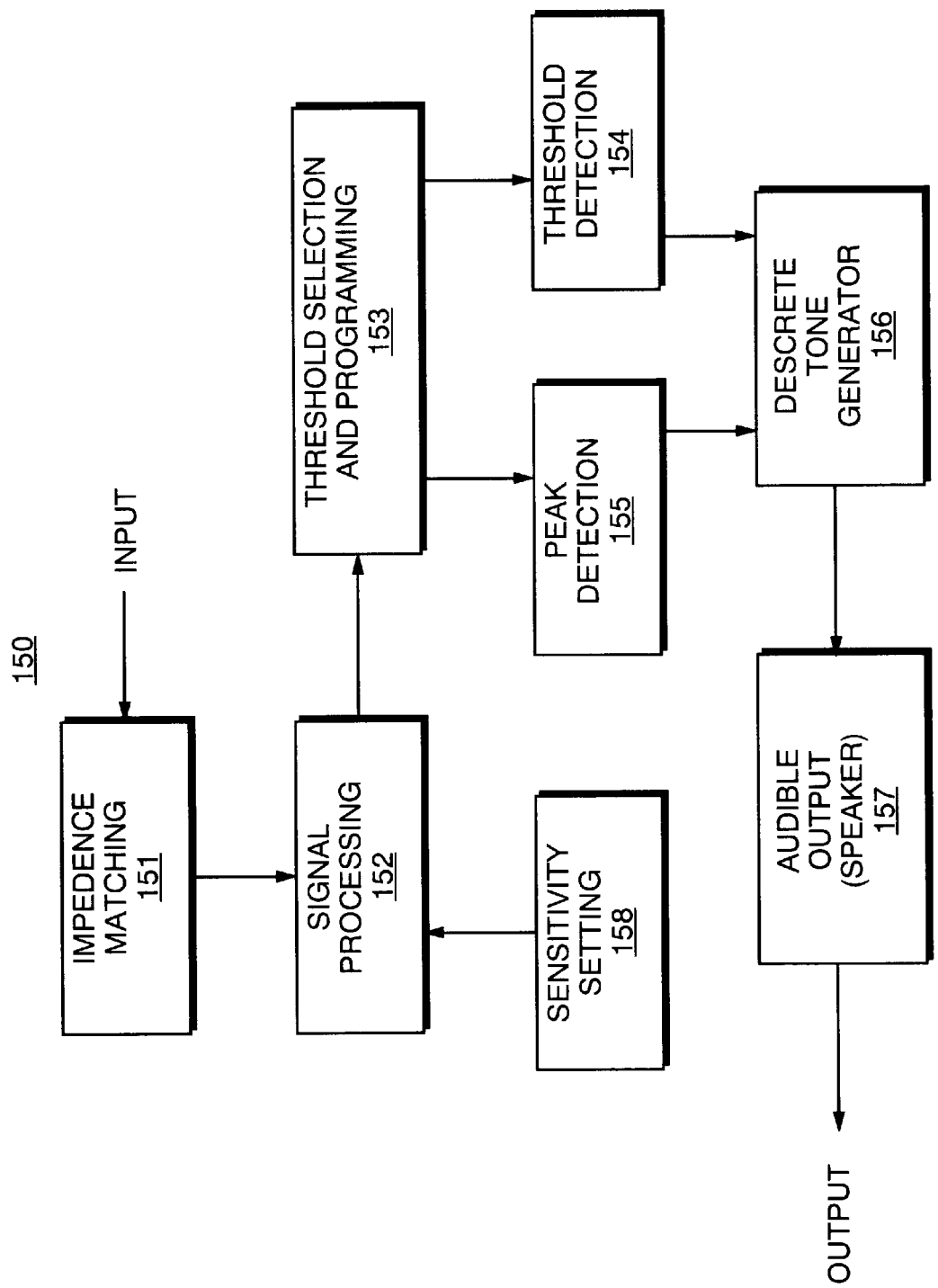
FIG. 15 is a block diagram of the signal processing and feedback circuit of the biofeedback module of FIG. 14, for which sensors of the invention provide input signal voltages.

Referring here to FIG. 15, a block diagram of the system to which the sensors are attached, is shown. An input signal from a sensor connects to impedance matching block 151, the output of block 151 is connected to signal processing block 152, which in turn connects to threshold selection and programming block 153. The output of block 153 feeds to both the threshold detection block 154 and the peak detection block 155, both block 154 and 155 outputs connect to the discrete tone generator block 156, which drives the audible output or speaker block 157. A sensitivity control block 158 allows the user to set the system gain and sensitivity by rotating the knob, the output of the sensitivity block 158 is connected to signal processor block 152 to accomplish this. The tone generator and audio output sections could equally well be a selectable light display/control circuit.

In operation, the system converts sensor inputs of motions detected, into multi-level audible or visual feedback. Research has demonstrated that the multi-level instant feedback has the attribute of providing a memorable history of an event that might otherwise be too fast to be able to make a connection between the desired effect and the feedback. The methodology of the system integration provides total measurement flexibility encompassing back and torso, as well as for limb joints and digits.

A large part of the gain of measurement flexibility comes from the concepts imbedded in the mounting appliance/transducer combination. Each system has a mounting appliance that supports all of the measurements that one would want to make for the wrist or the back or other points where complex motions are possible. The appliances are soft and comfortable to wear, they are fitted with coded attachment points for sensors or for other members of the mounting system; for example, an elastic suspender strap can be attach to a number of location on a belt or collar. The coding for the placement and orientation of the sensor on the mounting appliance might take the form of a Velcro strip upon which a mating Velcro strip affixed to the sensor can be aligned, or the use of placement marking which may be color coded can be incorporated into the mounting appliance, or the mounting appliance may be fitted with multiple pockets for the sensor to be fit into, where the selection of the pocket automatically selects the point of placement of the sensor and its orientation. The support electronics takes the form of a signal processing and feedback subsystem or module. The preferred unit, designed by this applicant and weighing only 1.4 ounces and being approximately 2"×2"×0.75" in size, can be attached directly to the clothing or to a convenient place on the sensor mounting subsystem.

The signal processing and feedback module can be factory set to have specific dynamic frequency response that helps to enhance the activity that is being targeted for training by sorting out "noise" motions that occur but are not a part of the training. The sensitivity of the electronics can be adjusted through a wide range to account for differences in application and to account for wide differences in skill level or motion capability of the user, as detected by the sensors.

The advantages of all of the subsystems described herein, including the mounting appliances, sensors claimed herein, and signal processing and feedback electronics, work together to meet the numerous larger objectives of the applicant.

The suspender system depends on a balance of compliant members to function properly, to this need, the compliant sensors described were invented. These elements convert low forces in the elastic suspender straps into a deformation of a half oval or full oval member, which can be instrumented with large area strain gages. A system that is easy to use, comfortable to wear and does not impede the performance of the activity results from the application of the principles.

The invention is susceptible of many embodiments. For example, there is within the scope of the invention, a low force, high compliance sensor assembly for monitoring a selected body motion on a human body, consisting of a large area flexible piezofilm sensor, the flexure of which creates a signal voltage. The sensor is connectible by any means, including electrical, optical and wireless, for transmitting the signal voltage to a suitable motion monitoring system. The sensor is mounted on the face of a larger area, semi-flexible backbone element so as to integrate localized strain anomalies being experienced at the mounting position on the human body, so that it can produce a coherent, useful, average signal voltage for the monitoring system. There may be included a compliant means for applying the sensor and backbone assembly in such manner to the human body that the selected body motion causes flexure of the backbone and piezofilm sensor combination, resulting in the generation of the desired signal voltage.

An example of a subset of the invention includes a low force, high compliance sensor system where the larger area semi-flexible backbone consists of a belt loop and compliant oval or circular member, where the compliant oval member is contained within the belt loop so as to hold it in a normally oval or circular shape. The belt loop may have two opposing end attach points to which external tension straps may be attached. There may be two piezofilm sensors attached to the face of the belt loop on opposing sides, substantially ninety degrees displaced from the attach points. The flexible belt loop may be placed in tension by its attach points with a suitable appliance, proximate the human body so as to be further tensioned by the selected body motion. The sum of the output of the sensors provides potentially improved resolution for the same motion as a single sensor.

An example of another subset of the invention is a low force, high compliance sensor system where the larger area, semi-flexible backbone consists of a compliant oval member, with a first two piezofilm sensors attached to the circumference of the oval member on opposing sides, and a second set of two piezofilm sensors is attached to the circumference of the oval member on opposing sides at substantially ninety degrees displacement from the first two sensors. There may be a suitable body appliance by which the oval member may be placed in compression on the axis of its first two sensors and in tension on the axis of its second two sensors, proximate the body and in position so as to be tensioned and compressed at its respective axes by the selected body motion.

An example of yet another subset of the invention is a low force, high compliance sensor system where the larger area semi-flexible backbone is a half-oval spring member, the end points of which are attachable to a body appliance such that when installed in light tension on the body, the half-oval spring member will be further tensioned by the selected body motion.

An example of still another example of a subset of the invention includes a low force, high compliance sensor system consisting of a top compliant pressure pad and a bottom compliant pressure pad, with a piezofilm sensor and backbone member being sandwiched or encased in between the pads. The bottom compliant pressure pad may have a fulcrum element imbedded within it, whether by alteration of density or application of an insert or other means, over which the sensor assembly are bendable, when the assemblage of sensor, backbone, and pads are inserted in a pocket such as on a belt, and placed in compression against the human body so as to be further compressed by the selected body motion.

An example of a further subset of the invention is a low force, high compliance sensor system applicable to bending motions of smaller body joints, where the large area semi-flexible backbone is configured with a central zone suitable for compliant bending over the joint. The central zone is interspersed between stiffer end zones, by which the sensor assembly is held by a suitable appliance proximate a smaller body joint such as a finger joint, with the central zone of the sensor assembly aligned over the joint.

An example of a still further subset of the invention includes a low force, high compliance sensor system where the larger area semi-flexible backbone is configured in the form of a flat trident, with a semi-flexible, longer central leg and two shorter, peripheral legs, forming a three tine fork by which the trident can be attached anywhere along the edge of a belt or band appliance by engaging the tines in the manner of a three tine paper clip, with the central leg or tine inside the belt or band, and the periphery tines outside the belt or band. A large area piezofilm sensor is affixed to the central leg, which can be inserted into a pocket in a belt type appliance proximate a body joint, with the sensor aligned over the joint.

As another example of the invention, there may be a low force, high compliance sensor system in combination with a motion monitoring and multi-step annunciator system which has means for emitting one single step announcement at a time, from among a limited set of step announcements, where each step announcement represents an incrementally greater amount of the selected body motion. The annunciator system may also have means for continuing for a period of up to 0.5 seconds, the emission of the specific step announcement triggered by the highest level of motion monitored in a motion cycle. The announcements may be in the form of a limited set of tones of stepped audio frequency, where each tone represents a different amount of body motion. Alternatively or in combination, the announcements may be in the form of a limited set of different colors of light, each color corresponding to a different amount of said body motion. The colors may be selected from among the group of colors including red, orange, yellow, green, blue, indigo, violet, and white.

Again alternatively, or in combination, the announcements may be in the form of a brief voice message, such as a number or word, from among a limited set of voice messages such as a set of spoken numbers like "one" through "five", or related words like "low", "medium", and "high", each message corresponding to a different amount of body motion. A voice announcement for a peak value, which could mean highest or lowest depending on the specific configuration and application, the voice announcement could be, or could be coupled with, a short phrase, such as "Warning, too high," or the like.

As a further example of the invention there may be a low force, high compliance sensor system that includes an absolute position overlay sensor, where the overlay sensor incorporates a limit switch, the output of the switch being connectible to a motion monitoring and multi-step annunciator system. The switch is connected to an actuating member which is attachable in such manner to the body so that when the selected body motion reaches a predetermined limit, it triggers the actuation of the switch and sense provides a static d.c., or zero reference indication to the monitoring and annunciator system, that may be useful for resetting or for integration with the signal voltage of the piezofilm sensor for other meaningful interpretation and announciation.

The sensors of the invention may be configured in any useful manner for transmission of the signal voltage to the monitoring and annunciator system, including the use of electrical leads between the sensor and the annunciator system; the use of photo-emitters, fiber optic bundles, and photo-detectors, and the use of a sensor connected transmitter, transmitting to an annunciator system connected receiver.

Other embodiments within the scope of the invention disclosed and the claims that follow, will be readily apparent to those skilled in the art.

What is claimed is:

1. A method for self teaching improvements in a selected repetitive kinetic body motion corprising the steps of
    using at least one body motion transducer applied to a preselecled location on the user's body corresponding to said selected repetitive kinetic body motion,
    dividing the full range of output of said transducer into a limited set of incremental ranges of body motion,
    associating each said incremental range with a different color from a limited set of colors,
    repetitively sensing the body position with said transducer throughout a full cycle of a said body motion,
    determining in which of said incremental ranges is the current body position, generating a visual feedback signal of the associated said color in real time within the user's view.

2. The method of claim 1, further comprising using a signal processing circuit and a remote visual feedback signal annunciator.

3. The method of claim 2, further comprising said signal processing circuit connected to said remote visual feedback signal annunicator by a wireless link.

4. The method of claim 1, further comprising the steps of
    sensing the end limit of said body motion in a given said cycle of body motion, and
    extending the duration of presentation of the specific visual feedback signal associated with the incremental range of the end limit position of said body motion.

5. The method of claim 1, further comprising the steps of
    sensing the end limit of said body motion in a given said cycle of body motion, and
    extending the duration of presentation of the specific visual feedback signal associated with the incremental range of the end limit position of said body motion for at least 0.1 seconds.

6. The method of claim 1, further comprising the steps of
    sensing the end limit of said body motion in a given said cycle of body motion, and
    extending the duration of presentation of the specific visual feedback signal associated with the incremental range of the end limit position of said body motion for at least 0.5 seconds.

7. The method of claim 1, said limited set of incremental ranges of body motion comprising 2 to 10 incremental ranges, said limited set of colors comprising 2 to 10 discrete colors.

8. The method of claim 1, said limited set of incremental ranges of body motion comprising 3 to 5 incremental ranges, said limited set of colors comprising 3 to 5 discrete colors.

9. The method of claim 1, said signal processing circuit comprising means for adjusting said incremental ranges with said full range of transducer output.

10. The method of claim 1, said visual signal annunciator comprising at least two different color LEDs.

11. The method of claim 1, said signal processing circuit further comprising feedback signal outputs connectable to a signal recording device.

12. The method of claim 1, said signal processing circuit further comprising audio feedback capability associated with said incremental ranges of said body motion.

13. The method of claim 12, said audio feedback capability comprising a limited set of discrete frequency tones.

14. The method of claim 12, said audio feedback capability comprising a limited set of different voice messages.

15. The method of claim 1, said transducer having a bandwidth inclusive of 0.1 to 40 Hertz.

16. The method of claim 1, said at least one transducer being multiple transducers, said signal processing circuit comprising means for integrating the outputs of said transducers and generating a composite body motion position relating to said selected repetitive kinetic body motion.

17. A system for self teaching improvements in a selected repetitive kinetic body motion comprising
    a colored light feedback annunciator connected to,
    a signal processing circuit connectable to at least one body motion transducer for continuously sensing body position through a cycle of said body motion, said signal processing circuit comprising
        means for dividing the full range output of said transducer into a limited set of incremental steps,
        means for associating a current body position with a discrete incremental step, each said incremental range associated with a discrete color, and
        means or generating said discrete color in real time at said feedback annunciator.

18. A system according to claim 17, further comprising a wireless link by which said signal processing circuit and said annunciator arc connected.

19. A system according to claim 17, said signal processing circuit further comprising means for identifying the limit of excursion of said body motion during said cycle and holding the associated discrete color on said feedback annunciator for an extended time thereafter.

20. A system according to claim 17, said at least one transducer comprising
    a large area flexible piezofilm sensor, the flexure of which creates a body position signal voltage,
    a larger area semi-flexible backbone, said sensor being attached to the face thereof so as to integrate localized strain anomalies and produce an average said signal voltage, and
    compliant means for applying said sensor and said backbone in such manner to user's body whereupon said selected body motion causes flexure of said backbone and said piezofilm sensor.

21. A system according to claim 20, said larger area semi-flexible backbone comprising a belt loop and compliant oval member, said compliant oval member contained within said belt loop so as to hold said belt loop in a normally oval shape, said belt loop having two opposing end attach points to which external tension straps may be attached said piezofilm sensor comprising two piezofilm sensors, said two sensors attached to the face of said belt loop on opposing sides substantially ninety degrees displaced from said attach points, said conciliating means comprising means by which said flexible belt loop may be placed in tension by said attach points proximate said human body so as to be further tensioned by said selected body motion.

22. A system according to claim 20, said larger area semi-flexible backbone comprising a compliant oval member, said piezofilm sensor comprising a first two piezofilm sensors, said first two sensors attached to the circumference of said compliant oval member on opposing sides, and a second two piezofilm sensors, said second two sensors attached to said circumference of said compliant oval member on opposing sides at substantially ninety degrees displaced from said first two sensors, said compliant means comprising means by which said oval member may be placed in compression on the axis of said first two sensors and in tension on the axis of said second two sensors and proximate said user's body so as to be tensioned and compressed at respective axes by said selected body motion.

* * * * *